United States Patent [19]
Pillers et al.

[11] Patent Number: 5,309,330
[45] Date of Patent: May 3, 1994

[54] LIGHT BOX

[75] Inventors: Russell B. Pillers, Sparks, Nev.; Darryl J. Bornhop, Truckee, Calif.; John B. Clayton; George H. Middle, both of Reno, Nev.

[73] Assignee: Citation Medical Corporation, Reno, Nev.

[21] Appl. No.: 2,924

[22] Filed: Jan. 11, 1993

[51] Int. Cl.$^5$ .............................................. F21V 8/00
[52] U.S. Cl. ...................................... 362/32; 385/53; 385/901
[58] Field of Search ................... 362/32; 385/53, 92, 385/93, 54, 88, 147, 43, 64, 66, 901

[56] References Cited

U.S. PATENT DOCUMENTS

| | | | |
|---|---|---|---|
| 4,232,934 | 11/1980 | Feinbloom | 385/92 |
| 4,566,763 | 1/1986 | Greguss | 359/725 |
| 4,589,404 | 5/1986 | Barath | 128/6 |
| 4,770,486 | 9/1988 | Wang et al. | 362/32 |
| 4,850,669 | 7/1989 | Welker et al. | 362/32 |
| 4,870,952 | 10/1989 | Martinez | 362/32 |
| 4,872,099 | 10/1989 | Kelley et al. | 362/295 |
| 4,986,622 | 1/1991 | Martinez | 362/32 |
| 5,037,421 | 8/1991 | Boutacoff | 606/15 |
| 5,099,399 | 3/1992 | Miller et al. | 362/32 |
| 5,230,555 | 7/1993 | Stephenson et al. | 362/32 |

Primary Examiner—Ira S. Lazarus
Assistant Examiner—L. Heyman
Attorney, Agent, or Firm—Nydegger & Associates

[57] ABSTRACT

The present invention provides a light box for fiber optic illumination cables. The light box includes a light bulb mounted in a disposable bulb holder. The light from the bulb enters a light preparation train including an aperture to produce an initial light beam, a hot mirror to reflect infrared and ultraviolet light, and an optical taper to narrow the light beam to the input diameter of the fiber optic illumination cable. The resulting light beam is passed to the illumination cable via a connector which selectively retains the fiber optic cable. The connector allows the cable to rotate while retained in the connector and includes a receiving tube surrounded by a sliding tube. A void between the tubes contains a plurality of ball retainers which can selectively extend through the wall of the receiving tube to retain the fiber optic cable. Because the connector is spring loaded, the cable is securely retained unless the sliding tube is manually moved into the releasing position by the operator. The light box further includes an electrical connector providing a safety circuit interrupting the power line to the light box when the drawer is removed, as well as a single use hour meter resetting circuit.

23 Claims, 3 Drawing Sheets

LIGHT BOX

TECHNICAL FIELD

The present invention pertains to illumination sources for fiber optic illumination cables. More particularly the present invention pertains to devices which provide high intensity light for surgical instruments which incorporate fiber optics. The present invention is particularly, but not exclusively, useful for providing light for endoscopes.

BACKGROUND OF THE INVENTION

Recently, modern medical techniques which are relatively non-invasive have been developed for viewing and performing different medical procedures on the interior structure of body parts. Medical instruments for performing these procedures are known generally as endoscopes and specifically include arthroscopes, spinalscopes, laproscopes, esophagoscopes and others. These instruments typically include a scope which is inserted into the body part to be examined. With an arthroscope, for example, the scope is coupled to a camera assembly and the camera assembly, in turn, is connected to a video display for generating a picture of the interior structure of the joint. Consequently, the operator of the arthroscope is able to view, in real-time, the interior structure of the body as the scope is inserted into the body. By viewing the internal body structure, a diagnosis can be made and appropriate treatment prescribed.

For illuminating the interior body structure, an endoscope assembly includes optical illumination fibers that terminate at the distal or viewing end of the scope and direct light into the body. The optical illumination fibers in turn, are coupled to a high intensity light source, or "light box" that includes a light bulb (i.e. xenon or metal halide). Such a light box, because of its size, power and control requirements is typically mounted externally to the probe and remotely from hand-held components of the endoscope. With an arthroscope, for instance, the scope portion of the endoscope and a portion of the camera assembly are mounted in a hand held housing, and the light box is external to this housing in a separate console. Such an arrangement necessitates a flexible light transmissive conduit which connects the external light box to the illumination fibers within the endoscope assembly. These types of light transmissive conduits must be precisely connected to the scope assembly and to the external light box. This requires precision design and construction of the endoscope assembly.

Existing light boxes have a number of drawbacks. First, the light boxes often have complicated connector assemblies which are necessary to connect the light box to the fiber optic illumination cable. One such connector is disclosed in U.S. Pat. No. 4,253,448 issued to Terada for an invention entitled "Endoscope Connector". The Terada connector fixably attaches the fiber optic cable to the light box and does not permit disconnection of the fiber optic cable from the light box.

Another plug and socket type connector is disclosed in U.S. Pat. No. 4,867,138 issued to Kubota et al. for an invention entitled "Rigid Electronic Endoscope". This connector while allowing the fiber optic cable to be disconnected from the light box, does not allow rotation of the cable relative to the light box. Further, accidental disconnection is possible because the plug is retained frictionally in its socket.

Yet another commonly used device for connecting an optic cable to a light box is a typical screw-in connector. A screw-in connector, however, does not permit quick connections and disconnections and does not allow rotation of the fiber optic cable relative to the light box once installed. Another commonly used connector is a single bearing retainer connector. This connector uses a single bearing in the socket to engage a groove in the plug to retain the plug in engagement with the socket. Consequently, the non-symmetrical force resulting from the single bearing often results in improper alignment between the light box and the cable.

Fiber optic light sources provide the required intensity of light by operating at high power levels. As a result, these high power levels reduce the life expectancy of the bulbs producing the light, which in turn necessitates periodic replacement of the bulbs. To prevent bulb failures during a surgical procedure, it is often desirable to replace the light bulb of a light box before it actually ceases providing light. In fact, many bulb manufacturers provide a maximum bulb use period and recommend replacing bulbs used longer than the maximum use period.

For this reason, some light boxes include an hour meter which allows the operator to monitor the operating time of the light box. For some light boxes, the resetting the hour meter when changing a bulb is complicated because the light box must be partially disassembled to reset the timer. Disassembly by untrained individuals can result in an electrical shock to the person and damage to the light box components. For these reasons, some manufacturers suggest sending the entire light box to the manufacturer. To avoid sending the light box to the manufacturer, many hour meters are never reset. Instead, the operator must note the meter reading at the time of bulb replacement and calculate the meter reading for the next bulb replacement.

Still another problem relating to the light box bulbs is the problem of replacing the bulb itself. For the light boxes to function optimally, it is crucial for the bulb to be correctly placed in the bulb holder to ensure proper alignment of the bulb on the optimum light path. Existing light boxes often have complicated assemblies which often require sending the light box to the manufacturer to ensure proper bulb alignment after bulb replacement.

In addition to above problems, light boxes often have a number of problems pertaining to the light produced by the light bulb. One problem is the heat produced in the light train as the light beam is narrowed to the input diameter of the fiber optic illumination cable. If too much heat is retained near the bulb, the life of the bulb can be reduced. Moreover, if too much heat is passed to the fiber optic cable, the cable may be damaged. Similarly, heat must be properly dissipated to prevent the connector itself from being heated to a point where physical handling becomes dangerous. Infrared and ultraviolet light components of the light produced by the bulb can damage both the tissue of the patient and the optical cable. For this reason, it is beneficial to prevent a portion of the infrared and ultraviolet wavelength components from reaching the fiber optic cable or the tissue. In light of the above, it is an object of the present invention to provide a light source incorporating a fiber optic cable connector which is uncomplicated. It is another object of the present invention to provide a light box including a connector which allows the fiber optic cable to be rotated relative to the light box. It is still another object of the present invention to provide a light box including a fiber optic cable connector which allows easy disconnection of the fiber optic cable from the light box while preventing accidental disconnection. Yet another object of the present invention is to provide a light box using a disposable bulb holder wherein the bulb can be correctly aligned by simple insertion of the holder into the light box. And yet another object of the present invention is to provide a light box using a bulb holder which automatically resets the hour meter of the light box during bulb replacement. Still further, it is an object of the present invention to provide a light box which maximizes heat dissipation and filters out undesirable light components prior to the produced light beam contacting the fiber optic cable. And further, it is an object of the present invention to provide a light source producing light having maximum intensity. Another object of the present invention is to provide a light box which is relatively easy to manufacture and which is comparatively economical.

SUMMARY OF THE INVENTION

The present invention provides a light box for fiber optic illumination cables. Generally, the light box includes a disposable bulb and bulb holder assembly, a fiber optic cable quick-connect and an improved light preparation train.

More specifically, the disposable light bulb is placed in a disposable bulb holder assembly. The bulb holder assembly includes a drawer member which is slidably installed in the light box. Attached to the drawer member is a disposable light bulb which is mounted and pre-aligned by the manufacturer.

Also attached to the drawer member is an electrical connector which cooperatively engages a mating connector mounted in the light box. The connectors are positioned such that electrical connections are made only if the drawer is properly installed in the light box. A safety circuit is connected to the connector on the drawer which disconnects the light box from the power supply when the drawer member is removed.

Still further, the disposable bulb holder assembly includes a fused circuit which is used to automatically reset an hour meter included in the light box. The hour meter of the light box is reset by a short-duration application of a current to a reset pin on the hour meter. The required current is applied by the fused circuit of a bulb holder assembly each time a new disposable assembly is installed in the light box and the electrical connector on the drawer member contacts the mating connector on the light box. Each bulb assembly can reset an hour meter only once because the fused circuit is designed to fail shortly after having power applied thereto. To accomplish this, the fuse in the fused circuit is sized to fail approximately one second after the drawer member is installed and power is applied to the circuit. In this manner, the fused circuit allows current to pass to the reset pin on the timer to reset the hour meter. After approximately one second, the fuse in the fused circuit fails and the then open circuit cannot again reset an hour meter.

Light from the bulb is channelled through a light preparation train to produce a final light beam having a final beam diameter. The resulting final light beam diameter is slightly larger than the input diameter of the fiber optic illumination cable. The light preparation train includes a series of component sections through which light from the bulb passes. During operation, light from the bulb passes through an aperture and a hot mirror which are components of the light preparation train. More particularly, the aperture physically prevents a portion of the light from impinging the fiber optic illumination cable. Further, the hot mirror allows the visible components of the light produced to pass through, but reflects the so called "hot" components of the light, namely, the infrared and ultraviolet light wavelength components. In this manner, both the aperture and the hot mirror help reduce the amount of heat in the light preparation train.

The light, having passed through the aperture and the hot mirror, is then passed through an optical taper to reduce the light beam diameter to the input diameter of the fiber optic illumination cable. A heat sink is attached to the optical taper to dissipate the heat produced in the optical taper because in the absence of the heat sink, the end of the illumination cable is subjected to elevated temperatures that may reduce the life of the cable.

A connector is provided on the light box which allows quick connection of a fiber optic illumination cable to the light box. The connector is a three ball retainer connector and includes an inner receiving tube which receives the fiber optic cable. Surrounding the receiving tube is an outer sliding tube which can longitudinally slide along the inner tube. Generally, the sliding tube is moved between two positions, a first or retaining position and a second or releasing position.

The inner surface of the sliding tube and the outer surface of the receiving tube leave an annular void which contains the three ball retainers. Further, the receiving tube is formed to include three holes which are symmetrically spaced around the periphery of the tube and through which the balls can partially extend. It is the position of the retaining balls which determines whether the fiber optic cable can be inserted into or removed from the connector.

The inner surface of the sliding tube is formed to include a sloped ridge which forces the balls into the holes in the receiving tube when the sliding tube is in the retaining position. Conversely, when the sliding tube is in the releasing position, the balls are no longer forced into the holes, instead the balls are allowed to move outward.

The fiber optic cable used with the present invention is formed to include, at its proximal end, a circumferential groove into which the ball retainers can extend. When the fiber optic cable is in the receiving tube and the balls partially extend through the receiving tube and into the recessed groove, the cable is prevented from moving in or out of the receiving tube. Because of the cooperative engagement between the ball retainers and the circumferential groove, the connector is still allowed to rotate within the connector. In this manner the connector is able to retain the fiber optic cable in the connector while allowing the cable to rotate relative to the light box.

Also located in the annular void between the receiving tube and the sliding tube is a helical spring which returns and maintains the sliding tube in the retaining position with a portion of the balls extending into the interior of the receiving tube. Accordingly, to insert or remove a fiber optic cable, the sliding tube must be manually moved against the action of the spring to the releasing position which allows the balls to move outward to clear the receiving tube. When the sliding tube is released, the spring then returns the sliding tube to the retaining position.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF PREFERRED EMBODIMENTS

Figure 1:
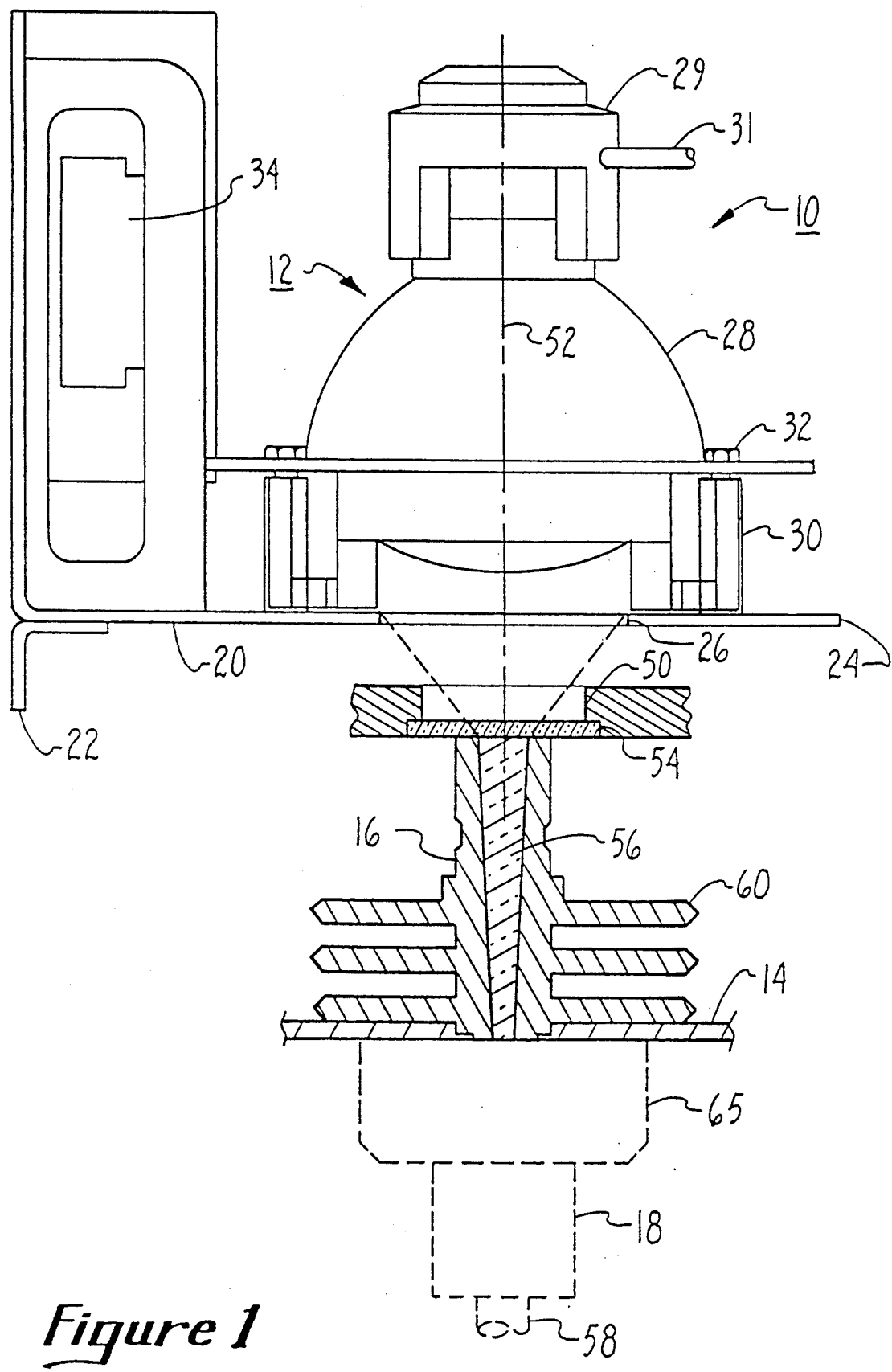
FIG. 1 is a partial cross-sectional view of the present invention including the disposable bulb assembly, light preparation train and fiber optic connector.

Referring initially to FIG. 1, the illumination system of the present invention is shown and generally designated 10. Generally, the system includes a disposable bulb assembly 12 slidably mountable in a housing 14. Connected to the housing is a light preparation train 16 and a fiber optic connector 18 (in phantom).

Figure 2:
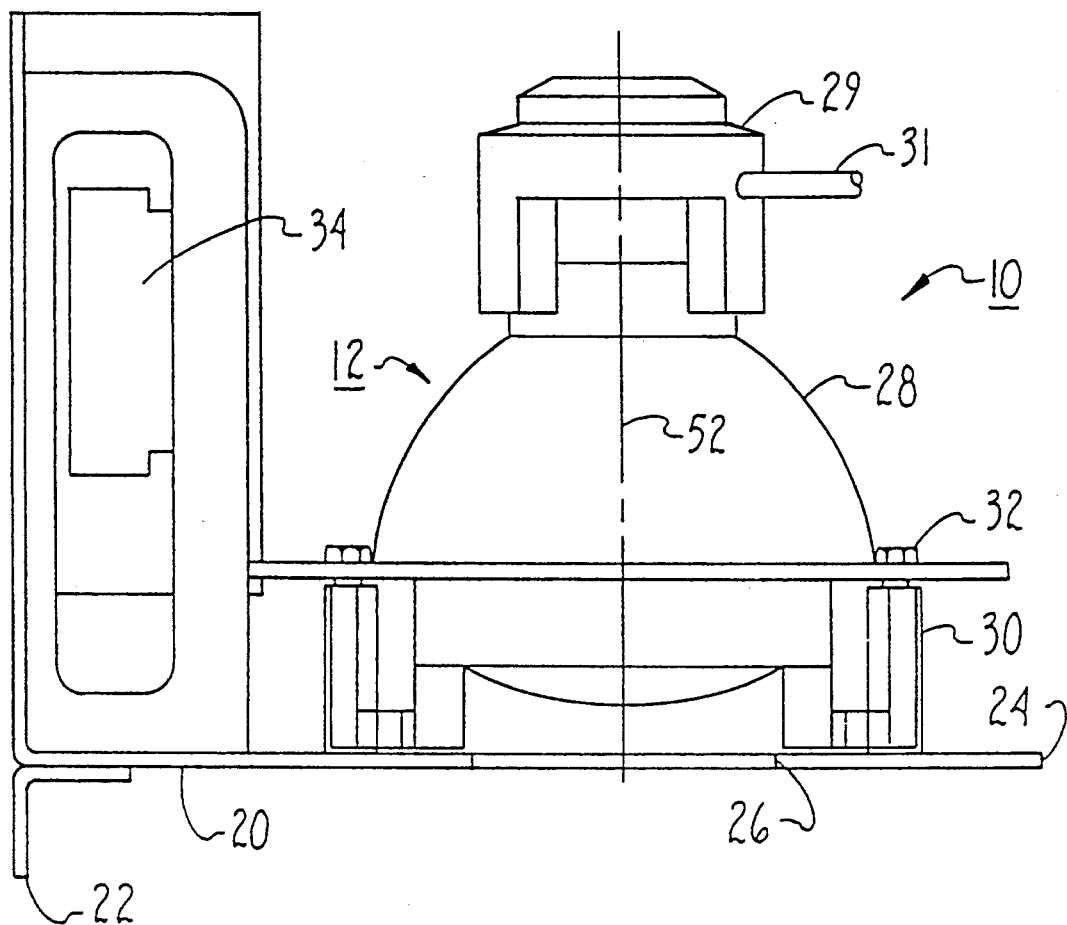
FIG. 2 is a front view of the disposable bulb assembly in isolation.

Referring now to FIG. 2, the disposable bulb assembly is depicted in isolation and generally designated 12. Drawer member 20 includes edge 22 and edge 24 which can be received by corresponding tracks mounted on the housing of the illumination device. Drawer member 20 is formed to include an opening 26 through which the light can pass.

Mounted on drawer member 20 is a bulb 28 which is separated from said drawer member by spacers 30 and is fastened to the drawer member by fasteners 32. Spacers 30 are generally cylindrical hollow tubes. Fasteners 32 can be screws or any other fastener capable of fixably attaching bulb 28 to drawer member 20. Attached to bulb 28 is bulb connector 29 which receives power from cable 31.

Also mounted on drawer member 20 is electrical drawer connector 34 which engages a mating plug mounted on the housing when the drawer member 20 is correctly installed in the housing. If the drawer member 20 is removed from the housing 14, or is incorrectly installed, the mating connectors cannot make contact.

Figure 3:
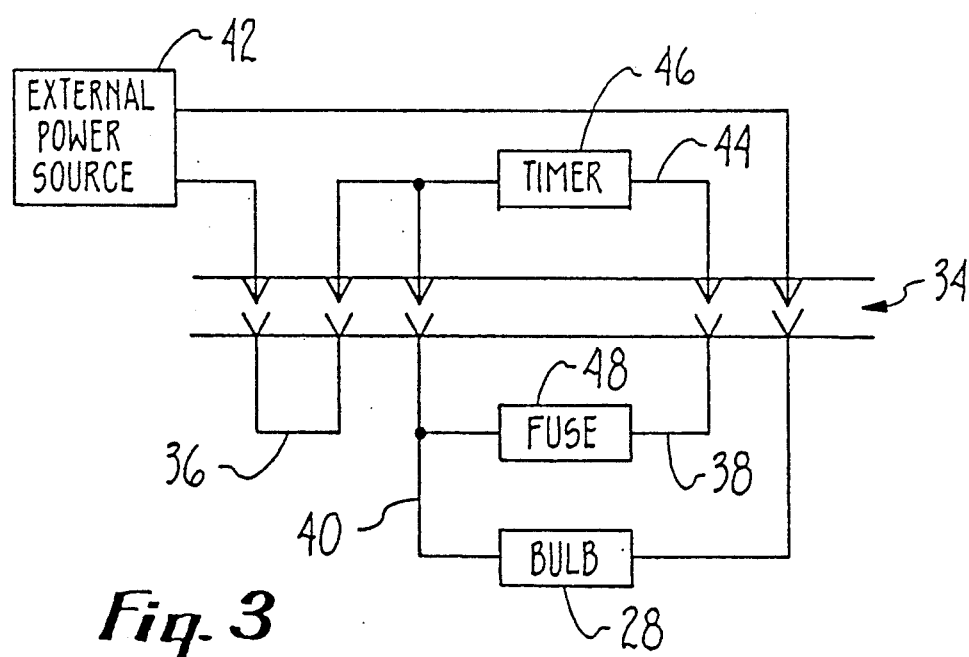
FIG. 3 is a block wiring diagram of the drawer connector and the other components of the present invention.

Referring now to FIG. 3, drawer connector 34 provides connections for a safety circuit 36, a fused circuit 38 and a bulb circuit 40. Safety circuit 36 is installed in the powerline of the system 10 and disconnects the illumination system 10 from its external power source 42 when the drawer 20 is not correctly installed. Bulb circuit 40 connects bulb 28 with the power source. Fused circuit 38 connects the reset pin 44 on timer 46 to the power source. Fuse 48 is sized to allow a current to flow from the power source to the timer reset pin 44 for approximately one second at which time the fuse 48 fails and the fused circuit 38 is broken.

Timer 46 is mounted on the housing 14 and indicates cumulative time since being reset. Timer 46 includes a reset pin 44, which when exposed to a 120 volt alternating current, resets the timer 46. It is to be appreciated that numerous voltages or currents could be used to reset the timer 46 without departing from the scope of the invention.

Referring back to FIG. 1, opening 26 in drawer member 20 allows light produced by the bulb assembly 12 to enter the light preparation train 16 at aperture 50. Light entering the light preparation train is substantially a light beam having a diameter substantially equal to the diameter of the aperture 50. This initial light beam travels along a light beam axis 52 which is coaxial with the longitudinal axis of the light preparation train 16. Aperture 50, installed in the light train, is sized to prevent a portion of the light produced by bulb 28 from entering the light preparation train 16. Light passing through aperture 50 impinges hot mirror 54 installed in the light train. Hot mirror 54 reflects infrared and ultraviolet light while allowing the remaining light to pass therethrough. Hot mirrors are well known and typically comprise a piece of glass covered by a reflective coating. As those skilled in the art will appreciate, it is equally permissible for the hot mirror 54 to be placed between the bulb 28 and the aperture 50 without departing from the scope of the invention.

Light passing through both the aperture 50 and the hot mirror 54 enters an optical taper 56 which reduces the diameter of the light beam until it is slightly larger than the input diameter of the fiber optic illumination cable 58. Having the light beam diameter slightly larger than the input diameter allows for minor misalignment between the light train and the fiber cable 58 without substantial decrease in performance. Optical taper 56 is enclosed by heat sink 60 which dissipates heat built up in the optical taper 56.

The final light beam passes through and exits the optical taper 56 which extends through the housing 14 and into fiber optic connector 18. The final light beam is comprised rays traveling in a direction which is substantially parallel to axis 52. This is important to ensure that the maximum number of light rays are in conformance with the numerical aperture (NA) of the fiber cable and therefore enter the fibers of the cable. As is known in the art:

$$NA = \sqrt{N_1^2 - N_2^2} \text{ where}$$

$N_1$ = Refractive Index of optic fiber core, and
$N_2$ = Refractive Index of optic fiber cladding.

Figure 4:
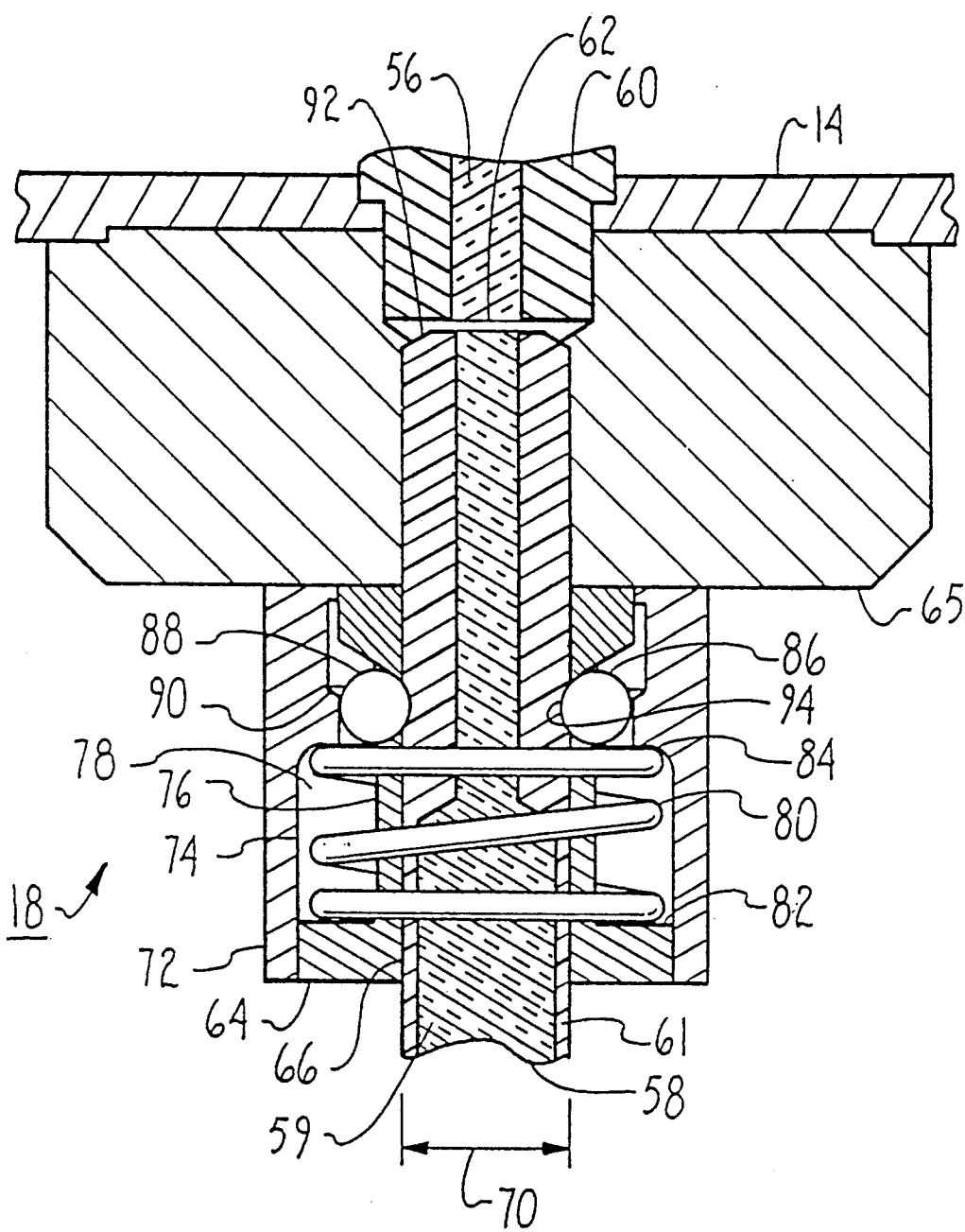
FIG. 4 is a partial cross-sectional view of the fiber optic connector assembly.

Referring now to FIG. 4, the fiber optic cable connector is shown and generally designated 18. Connector 18 includes a receiving tube 64 which is attached to the housing 14 via connector extension 65 by welding, bonding, screwing or other suitable means. Receiving tube 64 defines a socket 66 having a socket diameter which is slightly greater than the cable diameter 70 of the fiber optic illumination cable 58 Surrounding receiving tube 64 is sliding tube 72 which is able to slidingly reciprocate along the receiving tube 64. The inside surface 74 of the sliding tube 72 and the outer surface 76 of the receiving tube 64 are shaped to define an annular void 78 between the receiving tube 64 and the sliding tube 72.

Located in void 78 is a helical spring 80 which is compressed between shoulder 82 formed by receiving tube 64 and ridge 84 formed by sliding tube 72. Also located in void 78 are at least three symmetrically spaced balls 86 which are sized to partially extend through openings 88 formed by receiving tube 64. Openings 88 are preferably symmetrically spaced about the circumference of receiving tube 64.

Ridge 84 formed by sliding tube 72 includes a sloped portion 90 which forces balls 86 to partially extend through openings 88 when the sliding tube 72 is in the retaining position shown in FIG. 4. Manually moving the sliding tube 72 against the action of the spring and in a direction away from the housing 14 places sliding tube 72 in the releasing position. When the sliding tube is in the releasing position, balls 86 are allowed to retract into the void 78. Balls 86, when fully retracted into the void, do not extend into socket 66 of receiving tube 64, but still remain partially in the openings 88. Always remaining, at least partially, in openings 88 prevents balls 86 from freely moving about within void 78.

Cable 58 is well known to those skilled in the art and includes an optical fiber portion 59 and a surrounding strength member 61. When the fiber optic illumination cable 58 is placed in socket 66 and sliding tube 72 is in the retaining position, balls 86 are forced to extend partially into socket 66 and cooperatively engage cable 58 near its proximal end 92. More particularly, balls 86 engage a circumferential groove 94 formed near the proximal end 92 of the fiber optic cable 58. In this manner balls 86 retain cable 58 within socket 6 while allowing cable 58 to rotate relative to socket 66 and housing 14.

To insert the fiber optic illumination cable 58 into connector 18, sliding tube 72 is first manually pulled in a direction away from the housing 14 until it is in the releasing position. Cable 58 is then inserted into socket 66 until the sloped tip 96 of the proximal end 92 contacts balls 86 and pushes balls 86 into void 78. Cable 58 is continued to be inserted further into socket 66 until proximal end 92 is adjacent the end 62 of optical taper 56. Sliding tube 72 is then released and spring 80 returns the sliding tube 72 to the retaining position which, in turn, forces balls 86 into socket 66 and into groove 94 near proximal end 92.

While the particular fiber optic light box as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

What is claimed is:

1. A device for providing high intensity light to a fiber optic illumination cable having an outside diameter and a optical fiber portion having an input diameter, said device comprising;
   a housing;
   a light bulb for providing high intensity light, said bulb being mounted in a disposable bulb holder and said bulb holder being slidably mounted in said housing;
   a light preparation train for producing a final light beam from said high intensity light, said final light beam having a final light beam diameter slightly larger than said input diameter of said optical fiber portion of said fiber optic illumination cable, said light preparation train including an aperture, a hot mirror and an optical taper through which said high intensity light passes, said light preparation train being mounted in said housing and defining a light path axis; and
   means mounted in said housing along said light path axis for holding and aligning said optical fiber portion of said fiber optic illumination cable in optical communication with said light preparation train.

2. The device as recited in claim 1 wherein said aperture is sized to prevent a portion of said light from impinging said fiber optic illumination cable.

3. The device as recited in claim 2 wherein said hot mirror reflects infrared and ultraviolet light while allowing visible light to pass therethrough.

4. The device as recited in claim 3 wherein a portion of said light passes through said aperture and comprises an initial light beam having an initial light beam diameter, said optical taper converting said light beam having said initial light beam diameter to said light beam having said final light beam diameter.

5. The device as recited in claim 4 further comprising a heat sink attached to said optical taper to remove energy from said optical taper during operation of said device.

6. The device as recited in claim 5 wherein said hot mirror is intermediate said light bulb and said aperture.

7. The device as recited in claim 5 wherein said aperture is intermediate said light bulb and said hot mirror.

8. The device as recited in claim 1 wherein said disposable bulb holder further comprises;
   a drawer member having two edges slidingly engaging a drawer receiving means attached to said housing;
   a means attached to said drawer member for automatically resetting an hour meter attached to said housing when said bulb is installed in said device; and
   a means attached to said drawer member for disconnecting said device from a power supply when said disposable bulb member is removed from or incorrectly installed in said device.

9. The device as recited in claim 8 wherein said resetting means can reset said hour meter only once.

10. The device as recited in claim 9 wherein said hour meter includes a reset pin and said hour meter is reset when an alternating current is applied to said reset pin.

11. The device as recited in claim 10 where said resetting means is a power line including a fuse, said fuse being sized to allow said current to pass to said reset pin for less than 1 second before interrupting said power line, said power line being connected to said power supply only when said drawer is correctly installed in said device.

12. The device as recited in claim 11 wherein said means for disconnecting comprises a safety circuit installed in a power line for said device, said circuit being connected to an electrical connector between said drawer member and said housing, said electrical connector opening said safety circuit when said drawer member is removed from said housing.

13. The device as recited in claim 1 wherein said holding and aligning means comprises;
   a generally cylindrical receiving tube connected to said housing, said receiving tube defining a longitudinal axis coaxial with said light path axis, said receiving tube having two ends, a body portion, and an inside diameter slightly larger than said outside diameter of said fiber optic illumination cable; and
   a means mounted on said receiving tube for selectively retaining said fiber optic illumination cable in said receiving tube, said retaining means allowing rotation of said fiber optic illumination cable about said longitudinal axis while retaining said fiber optic illumination cable in said receiving tube.

14. The device as recited in claim 13 wherein said body portion of said receiving tube is formed to include a plurality of openings, said fiber optic illumination cable has a proximal end forming a circumferential groove thereon, and said retaining means comprises;
- a generally cylindrical sliding tube coaxial with and surrounding said receiving tube, said sliding tube having a retaining position and a releasing position, said receiving tube and said sliding tube being shaped to leave an annular void therebetween;
- a plurality of substantially spherical balls located in said annular void, said balls being forced by said sliding tube to partially extend through said openings to engage said groove when said sliding tube is in said retaining position; and
- a helical spring positioned in said annular void, said spring being compressed by an inwardly extending ridge formed by said sliding tube and an outwardly extending shoulder formed by said receiving tube, said spring urging said sliding tube toward said retaining position.

15. The device as recited in claim 14 wherein said sliding tube is formed to allow said balls to move outward to release said fiber optic illumination cable when said sliding tube is in said releasing position.

16. The device as recited in claim 14 wherein said receiving tube forms at least three openings and said retaining means comprises at least three spherical balls.

17. A device for providing high intensity light to a fiber optic illumination cable, said cable having an outside diameter, an input diameter defined within said outside diameter, and a proximal end formed to include a circumferential groove, said device comprising;
- a light bulb providing high intensity light mounted in a bulb holder;
- a light preparation train connected to said bulb holder to allow light produced by said light bulb to enter said light preparation train, said light preparation train producing final light beam from said high intensity light, said final light beam having a final light beam diameter slightly larger than said input diameter of said fiber optic illumination cable, said light preparation train defining a light path axis; and
- a fiber optic cable connector attached to said light preparation train to selectively connect said fiber optic illumination cable to said light preparation train, said connector comprising;
- a generally cylindrical receiving tube connected to said light preparation train, said receiving tube defining a longitudinal axis coaxial with said light path axis, said receiving tube being formed with a plurality of openings and having two ends, a body portion, and an inside diameter slightly larger than said outside diameter of said fiber optic illumination cable;
- a generally cylindrical sliding tube coaxially surrounding said receiving tube, said sliding tube having a retaining position and a releasing position, said receiving tube and said sliding tube being shaped to leave an annular void therebetween;
- a plurality of substantially spherical balls located in said annular void, said balls being forced by said sliding tube to partially extend through said openings to engage said groove when said sliding tube is in said retaining position; and
- a helical spring positioned in said annular void, said spring being compressed between an inwardly extending ridge formed by said sliding tube and an outwardly extending shoulder formed by said receiving tube, said spring urging said sliding tube toward said retaining position.

18. The device as recited in claim 17 wherein said sliding tube is formed to allow said balls to move outward to release said fiber optic illumination cable when said sliding tube is in said releasing position.

19. The device as recited in claim 18 wherein said receiving tube forms at least three openings and said retaining means comprises at least three spherical balls.

20. The device as recited in claim 19 said light preparation train comprising an aperture, a hot mirror and an optical taper through which said light passes.

21. The device as recited in claim 20 wherein said aperture is sized to prevent a portion of said light from impinging said fiber optic illumination cable.

22. The device as recited in claim 21 wherein said hot mirror reflects infrared and ultraviolet light while allowing visible light to pass therethrough.

23. The device as recited in claim 22 wherein a portion of said light passes through said aperture and comprises an initial light beam having an initial light beam diameter, said optical taper converting said light beam having said initial light beam diameter to said light beam having said final light beam diameter.

* * * * *